United States Patent [19]
Van Gemert et al.

[11] Patent Number: 5,637,262
[45] Date of Patent: Jun. 10, 1997

[54] PHOTOCHROMIC SUBSTITUTED NAPHTHOPYRAN COMPOUNDS

[75] Inventors: Barry Van Gemert, Murrysville; Anil Kumar, Pittsburgh, both of Pa.

[73] Assignee: Transitions Optical, Inc., Pinellas Park, Fla.

[21] Appl. No.: 454,784

[22] Filed: May 31, 1995

Related U.S. Application Data

[62] Division of Ser. No. 30,246, Jun. 21, 1993, Pat. No. 5,466,398.

[51] Int. Cl.$^6$ ............... G02B 5/23; G02B 27/00; C07D 311/92; C07D 407/04
[52] U.S. Cl. ............... 252/586; 549/389; 549/60; 549/32; 548/525; 548/454; 548/407; 548/364.1; 548/311.4; 546/196; 546/15; 546/272.7; 546/275.7; 546/276.4; 546/277.4; 546/282.7; 524/110; 524/106; 524/105; 524/102; 524/90; 524/84
[58] Field of Search ............... 549/331, 389, 549/60, 32; 548/525, 454, 407, 364.1, 311.4; 546/269, 196, 15; 252/586; 524/110, 106, 105, 102, 90, 84

[56] References Cited

U.S. PATENT DOCUMENTS

| | | | |
|---|---|---|---|
| 3,562,172 | 2/1971 | Ono et al. | 252/300 |
| 3,567,605 | 3/1971 | Becker | 204/158 |
| 3,578,602 | 5/1971 | Ono et al. | 252/300 |
| 3,627,690 | 12/1971 | Casella et al. | 252/300 |
| 4,215,010 | 7/1980 | Hovey et al. | 252/300 |
| 4,342,668 | 8/1982 | Hovey et al. | 252/586 |
| 4,637,698 | 1/1987 | Kwak et al. | 351/163 |
| 4,720,356 | 1/1988 | Cu | 252/586 |
| 4,816,584 | 3/1989 | Kwak et al. | 544/71 |
| 4,818,096 | 4/1989 | Heller et al. | 351/163 |
| 4,826,977 | 5/1989 | Heller et al. | 544/70 |
| 5,066,818 | 11/1991 | Gemert | 549/389 |
| 5,200,116 | 4/1993 | Heller | 252/586 |
| 5,238,981 | 8/1993 | Knowles | 524/110 |

FOREIGN PATENT DOCUMENTS 816719  8/1937  France.

OTHER PUBLICATIONS

George A. Olah, *Friedel–Crafts and Related Reactions*, Interscience Publishers, vol. 3, Chap. XXXI, pp 1–8, 82–88, 1964.
"1,8,17,24–Tetroxa[8.8] (2,6)naphthalenophane–3,5,19, 21–tetrayne–10,30–dicarboxylic Acid Derivatives", Novel Complexors of Aromatic Guests, Esa T. Jarvi et al, J. Am Chem. Soc. 1982, 104, 7196–7204.

*Primary Examiner*—Nicky Chan
*Attorney, Agent, or Firm*—Irwin M. Stein; Frank P. Mallak

[57] ABSTRACT

Described are novel reversible photochromic 3H-naphtho[2,1-b]pyran compounds, of the following graphic formula:

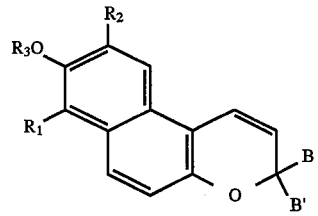

wherein $R_1$ is hydrogen or alkyl, $R_2$ is hydrogen or preferably a carboalkoxy group and $R_3$ is hydrogen or preferably an alkyl group, provided that either $R_1$ or $R_2$ is hydrogen, and B and B' are the aryl groups phenyl or naphthyl, a heterocyclic aromatic group or together form a spiro adamantylene group. Also described are organic host materials that contain or that are coated with such compounds. Articles such as ophthalmic lenses or other plastic transparencies that incorporate the novel naphthopyran compounds or combinations thereof with complementary photochromic compounds, e.g., spiro(oxazine) type compounds, are also described.

21 Claims, No Drawings

PHOTOCHROMIC SUBSTITUTED NAPHTHOPYRAN COMPOUNDS

This is a division of application Ser. No. 08/080,246, filed Jun. 21, 1993, now U.S. Pat. No. 5,466,398.

DESCRIPTION OF THE INVENTION

The present invention relates to certain novel naphthopyran compounds. More particularly, this invention relates to novel photochromic naphthopyran compounds and to compositions and articles containing such novel naphthopyran compounds. When exposed to light radiation involving ultraviolet rays, such as the ultraviolet radiation in sunlight or the light of a mercury lamp, many photochromic compounds exhibit a reversible change in color. When the ultraviolet radiation is discontinued, such a photochromic compound will return to its original color or colorless state.

Various classes of photochromic compounds have been synthesized and suggested for use in applications in which a sunlight-induced reversible color change or darkening is desired. U.S. Pat. No. 3,567,605 (Becker) describes a series of pyran derivatives, including certain benzopyrans and naphthopyrans. These compounds are described as derivatives of chromene and are reported to undergo a color change, e.g., from colorless to yellow-orange, on irradiation by ultraviolet light at temperatures below about −30° C. Irradiation of these compounds with visible light or upon raising the temperature to above about 0° C. is reported to reverse the coloration to a colorless state.

The present invention relates to novel 3H-naphtho[2,1-b] pyran compounds having certain substituents at the number 8 carbon atom and certain substituents either at the number 7 or number 9 carbon atom of the naphthopyran. These compounds have been found to have an improved solar response and an unexpectedly higher activating wavelength than corresponding compounds having no substituents on the naphtho portion of the naphthopyran or a substituent at the number 8 carbon atom. As discussed later, the number 7, 8 and 9 carbon atoms of 3H-naphtho[2,1-b]pyran compounds are part of the naphtho portion of the naphthopyran.

DETAILED DESCRIPTION OF THE INVENTION

In recent years, photochromic plastic materials, particularly plastic materials for optical applications, have been the subject of considerable attention. In particular, photochromic ophthalmic plastic lenses have been investigated because of the weight advantage they offer, vis-a-vis, glass lenses. Moreover, photochromic transparencies for vehicles, such as cars and airplanes, have been of interest because of the potential safety features that such transparencies offer.

Photochromic compounds useful in optical applications, such as conventional ophthalmic lenses, are those which possess (a) a high quantum efficiency for coloring in the near ultraviolet, (b) a low quantum yield for bleaching with white light, and (c) a relatively fast thermal fade at ambient temperature but not so rapid a thermal fade rate that the combination of white light bleaching and thermal fade prevent coloring by the ultraviolet component of strong sunlight. In addition, the aforesaid properties are desirably retained in conventional rigid synthetic plastic materials customarily used for ophthalmic and plano lenses when such materials have applied to or incorporated therein such photochromic compounds.

Another factor regarding the selection of potential photochromic compounds for optical applications is their response under a variety of solar conditions, e.g., a full mid-day sun, or the more highly filtered solar rays found early or late in the day. Ideally, photochromic compounds respond equally well under these differing conditions. Such a variety of solar conditions can be simulated on an optical bench with a Xenon lamp fitted with either a 320 nanometer or a 360 nanometer cutoff filter. Preferred photochromic compounds are those that have a minimal difference in optical density after exposure to both wavelength ranges of ultraviolet light. The ultraviolet light having a wavelength higher than 360 nanometer represents low light conditions that occur early or late in the day when the shorter wavelength components of the UV spectrum are attenuated.

In accordance with the present invention, it has been discovered that certain novel 3H-naphtho[2,1-b]pyran compounds having a high quantum efficiency for coloring in the near ultraviolet and an acceptable rate of fade may be prepared. These compounds also have improved solar response levels as compared to other substituted and unsubstituted naphthopyran compounds. This attribute resolves a problem that has been found with other photochromic compounds of reduced photochromic response in low light conditions that occur early or late in the day.

The compounds of the present invention may be described as 3H-naphtho[2,1-b]pyrans that are substituted with an oxy-bearing substituent at the number 8 carbon atom and with either an alkyl group at the number 7 carbon atom or with a carbonyl bearing substituent at the number 9 carbon atom. These naphthopyran compounds may be represented by the following graphic formula:

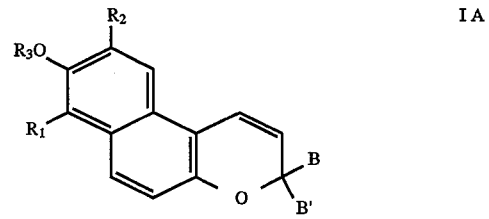

In graphic formula I A, $R_1$ may be hydrogen or a $C_1$–$C_6$ alkyl, e.g., methyl, ethyl, propyl, n-butyl, iso-butyl, n-amyl, iso-amyl, hexyl, etc. Preferably, $R_1$ is hydrogen or $C_1$–$C_3$ alkyl, e.g., methyl. $R_2$ may be hydrogen or the group, —C(O)W, W being —OR$_4$ or —N(R$_5$)R$_6$, wherein $R_4$ may be hydrogen, allyl, $C_1$–$C_6$ alkyl, e.g., methyl, ethyl, propyl, isopropyl, n-butyl, iso-butyl, sec-butyl, amyl, hexyl, etc., phenyl, $C_1$–$C_6$ monoalkyl substituted phenyl, e.g., tolyl, cumenyl, etc., $C_1$–$C_6$ monoalkoxy substituted phenyl, e.g., anisyl, ethoxyphenyl, etc., phenyl($C_1$–$C_3$)alkyl, e.g., benzyl, phenethyl, 3-phenylpropyl, etc., $C_1$–$C_6$ monoalkyl substituted phenyl($C_1$–$C_3$)alkyl, $C_1$–$C_6$ monoalkoxy substituted phenyl($C_1$–$C_3$)alkyl, $C_1$–$C_6$ alkoxy($C_2$–$C_4$)alkyl, or $C_1$–$C_6$ monohaloalkyl, and wherein $R_5$ and $R_6$ each may be selected from the group consisting of hydrogen, $C_1$–$C_6$ alkyl, $C_5$–$C_7$ cycloalkyl, phenyl and mono- or di-substituted phenyl, or $R_5$ and $R_6$ together with the attached nitrogen atom form an indolinyl group or a mono- or di-substituted or unsubstituted, non-aromatic, saturated, or unsaturated heterocyclic ring containing from 5 to 6 ring atoms, which ring includes as the hetero atom said nitrogen atom alone or one additional hetero atom of nitrogen or oxygen, e.g., morpholino, piperidino, 1-pyrrolidyl, 1-pyrrolinyl, 1-imidazolidyl, 2-imidazolin-1-yl, 2-pyrazolidyl, 1-piperazinyl, etc., said phenyl and heterocyclic ring substituents being selected from $C_1$–$C_6$ alkyl and $C_1$–$C_6$ alkoxy, said halo substituent being chloro or fluoro. Preferably, $R_2$ is hydrogen or the group, —C(O)W, W being —OR$_4$, and wherein $R_4$ is a $C_1-C_3$ alkyl or allyl. In graphic formula I A, either $R_1$ or $R_2$ is hydrogen.

$R_3$ in graphic formula I A may be hydrogen, $C_1-C_6$ alkyl, phenyl($C_1-C_3$)alkyl, $C_1-C_6$ monoalkyl substituted phenyl ($C_1-C_3$)alkyl, $C_1-C_6$ monoalkoxy substituted phenyl ($C_1-C_3$)alkyl, $C_1-C_6$ alkoxy($C_2-C_4$)alkyl, $C_5-C_7$ cycloalkyl, $C_1-C_4$ monoalkyl substituted $C_5-C_7$ cycloalkyl, $C_1-C_6$ monohaloalkyl, allyl or the group, —C(O)X, wherein X may be $C_1-C_6$ alkyl, phenyl, $C_1-C_6$ mono- or $C_1-C_6$ di-alkyl substituted phenyl, $C_1-C_6$ mono- or $C_1-C_6$ di-alkoxy substituted phenyl, $C_1-C_6$ alkoxy, phenoxy, $C_1-C_6$ mono- or $C_1-C_6$ di-alkyl substituted phenoxy, $C_1-C_6$ mono- or $C_1-C_6$ di-alkoxy substituted phenoxy, $C_1-C_6$ alkylamino, phenylamino, $C_1-C_6$ mono- or $C_1-C_6$ di-alkyl substituted phenylamino, or $C_1-C_6$ mono- or $C_1-C_6$ di-alkoxy substituted phenylamino, said halo substituent being chloro, fluoro, or bromo. Preferably, $R_3$ is hydrogen, $C_1-C_3$ alkyl, phenyl($C_1-C_3$)alkyl, or the group, —C(O)X, wherein X is a $C_1-C_4$ alkyl.

In graphic formula I A, B and B' may each be selected from the group consisting of (i) the substituted or unsubstituted aryl groups phenyl and naphthyl, (ii) the substituted or unsubstituted heterocyclic aromatic groups pyridyl, furyl, benzofuryl, thienyl, benzothienyl, and (iii) B and B' taken together form the spiro adamantylene group. The aryl and heterocyclic substituents of B and B' may each be selected from the group consisting of hydroxy, $C_1-C_5$ alkyl, $C_1-C_5$ haloalkyl, $C_1-C_5$ alkoxy, $C_1-C_5$ alkoxy($C_1-C_4$)alkyl, $C_1-C_5$ dialkylamino, acryloxy, methacryloxy, and halogen, said halogen or (halo) groups being fluoro, chloro, or bromo, provided that at least one of B and B' is a substituted or unsubstituted phenyl, except when B and B' form the spiro adamantylene group.

Preferably, B and B' are represented respectively by the following graphic formulae:

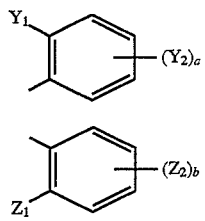

wherein, $Y_1$ may be selected from the group consisting of $C_1-C_5$ alkyl, $C_1-C_5$ alkoxy, fluoro, and chloro; $Z_1$ may be selected from the group consisting of hydrogen and $Y_1$; each $Y_2$ and $Z_2$ are selected from the group consisting of $C_1-C_5$ alkyl, $C_1-C_5$ alkoxy, hydroxy, halogen, e.g., chloro, fluoro, and bromo, acryloxy, and methacryloxy, and a and b are each integers of from 0 to 2. Preferably, $Y_1$ is $C_1-C_3$ alkyl, $C_1-C_3$ alkoxy, or fluoro, $Z_1$ is hydrogen, each $Y_2$ and $Z_2$ is selected from the group consisting of $C_1-C_3$ alkyl and $C_1-C_3$ alkoxy, a is the integer 0 or 1, and b is an integer from 0 to 2.

The preferred naphthopyrans of the present invention are represented in the following graphic formula I B, which also shows the numbering of the ring atoms:

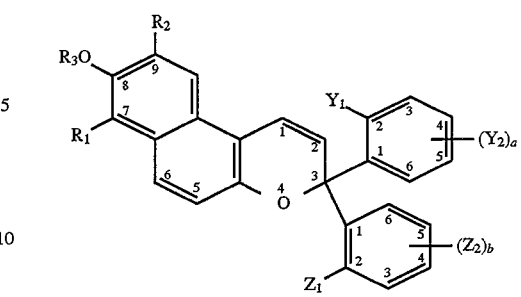

Compounds represented by graphic formula I C are prepared by a coupling reaction followed by derivatization as shown in Reaction C. The propargyl alcohol represented by graphic formula VI, which is used in Reaction C, may be prepared by methods described in Reaction A and Reaction B. The substituted naphthalene diol, represented by graphic formula VII A, which is used in Reaction C, may be prepared by a method described hereinafter. The substituted naphthol represented by graphic formula VII B, that is used in Reaction E to make the compounds represented by graphic formula I D may be prepared by the methods described in Reaction D.

Benzophenone compounds represented by graphic formula V shown in Reaction A may be purchased from fine chemical manufacturers, custom synthesized or may be prepared by Friedel-Crafts methods using an appropriately substituted or unsubstituted benzoyl chloride of graphic formula IV and a commercially available substituted benzene compound of graphic formula III. See the publication, *Friedel-Crafts and Related Reactions*, George A. Olah, Interscience Publishers, 1964, Vol. 3, Chapter XXXI (Aromatic Ketone Synthesis).

In Reaction A, the compounds represented by graphic formulae III and IV are dissolved in a solvent, such as carbon disulfide or methylene chloride, and reacted in the presence of a Lewis acid, such as aluminum chloride, to form the corresponding benzophenone represented by graphic formula V.

REACTION A

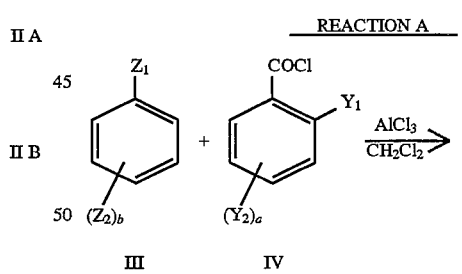

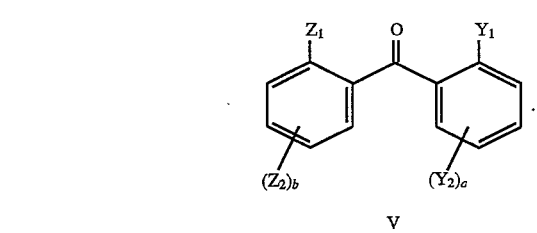

In Reaction B, the substituted benzophenone represented by graphic formula V is reacted with sodium acetylide in a suitable solvent, such as dry tetrahydrofuran (THF), to form the corresponding propargyl alcohol, which may be represented by graphic formula VI.

REACTION B

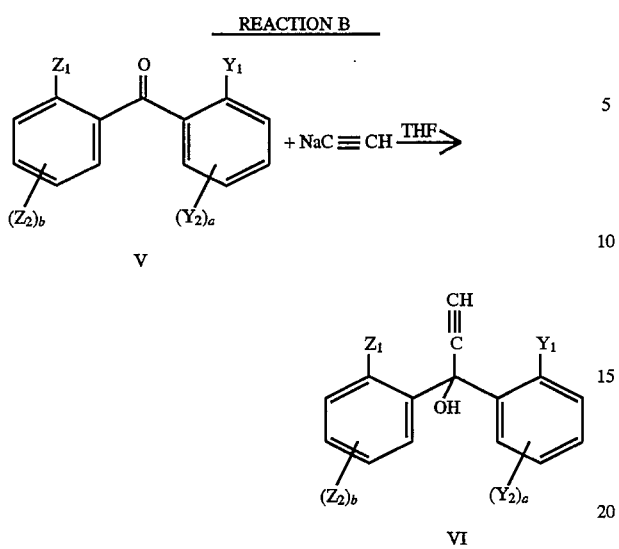

In Reaction C, the propargyl alcohol represented by graphic formula VI is coupled with a 7-substituted 2,6-naphthalene diol, represented by graphic formula VII A, under acidic conditions to form the naphthopyran of graphic formula VIII A. 7-substituted 2,6-naphthalene diol e.g., 2,6-dihydroxy-7-carbomethoxynaphthalene can be prepared by methods described for the synthesis of n-hexyl-3,7-dihydroxy-2-naphthoate described in the Journal of the American Chemical Society 104, pages 7196 to 7204, 1982.

In order to make the compound represented by graphic formula I C, it is necessary to derivatize, i.e., acylate, methylate, benzylate, etc., the hydroxyl group on the number 8 carbon atom of the naphthopyran represented by graphic formula VIII A. This is accomplished by reaction of the hydroxyl group with an alkyl or aroyl halide, chloroformate, isocyanate, etc.

REACTION C

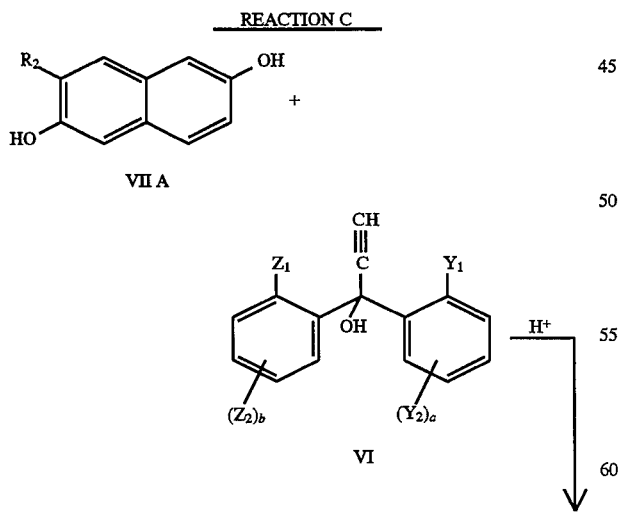

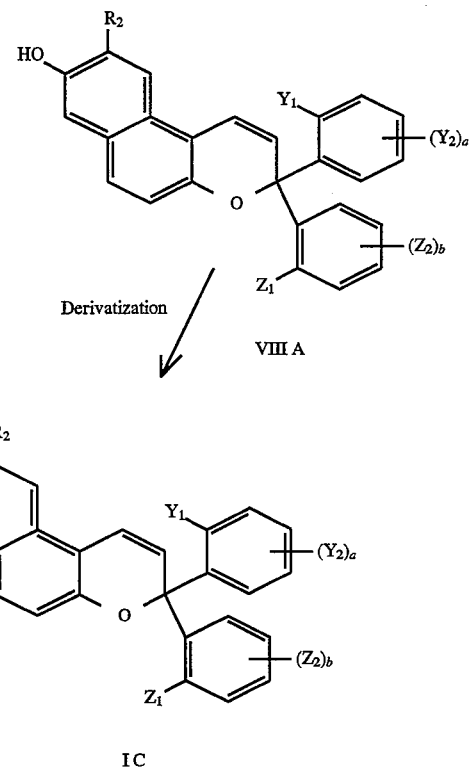

In Reaction D, the naphthaldehyde or alkyl aryl ketone represented by graphic formulae IX A and IX B respectively, is reduced using the Wolff-Kishner process to yield the compound represented by graphic formula X, which can be selectively brominated to yield the bromonaphthalene compound of graphic formula XI. This compound may be subjected to high pressure copper mediated solvolysis to produce the substituted naphthol represented by graphic formula XII followed by demethylation to produce the substituted naphthol represented by graphic formula VII B. The various compounds prepared in this series of reactions may be commercially available from fine chemical manufacturers or may be custom synthesized.

REACTION D

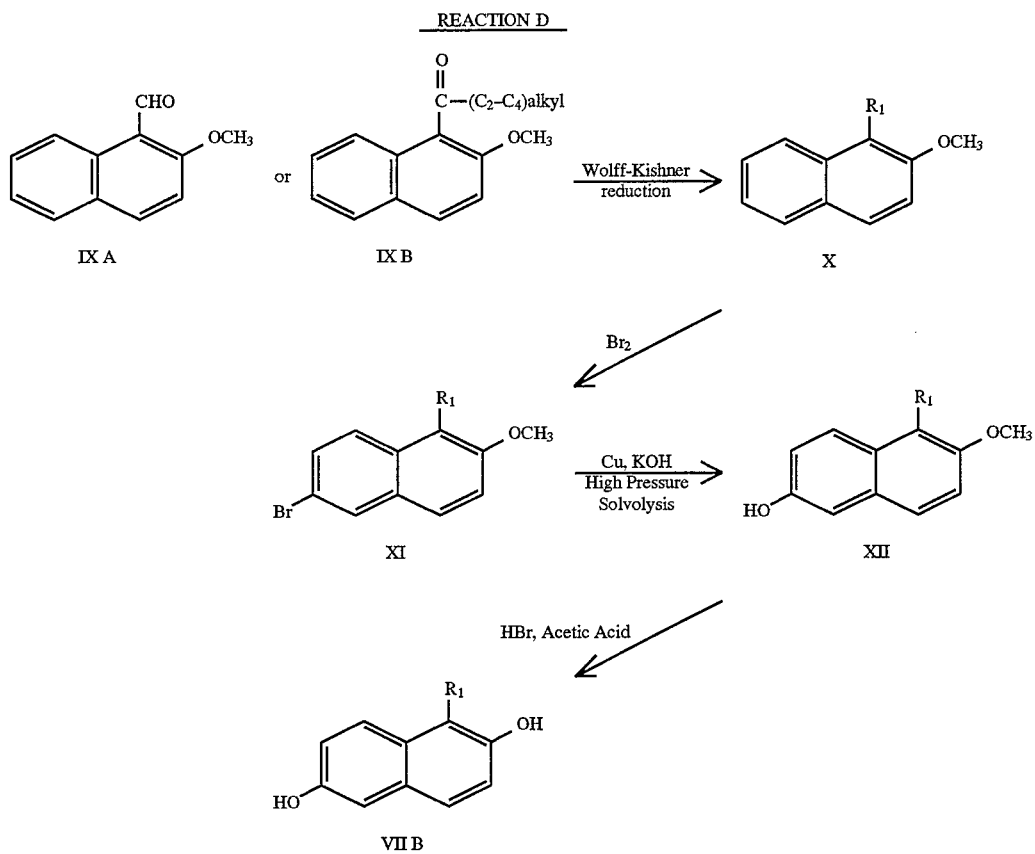

In Reaction E, the propargyl alcohol represented by graphic formula VI is coupled with a substituted naphthol of graphic formula VII B under acidic conditions to form the naphthopyran of graphic formula VIII B. The compound represented by graphic formula I D is produced by derivatizing the hydroxyl group on the number 8 carbon atom of the naphthopyran compound represented by graphic formula VIII B in an identical manner as previously discussed for Reaction C. If $R_3$ is methyl, the compound represented by graphic formula XII in Reaction D may be used directly in place of the compound represented by VII B in Reaction E.

REACTION E

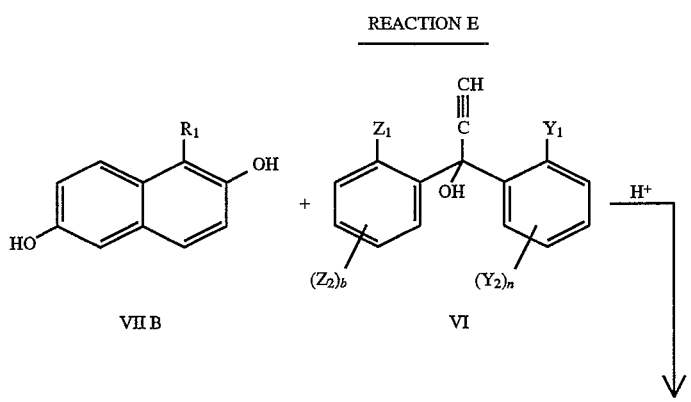

-continued
REACTION E

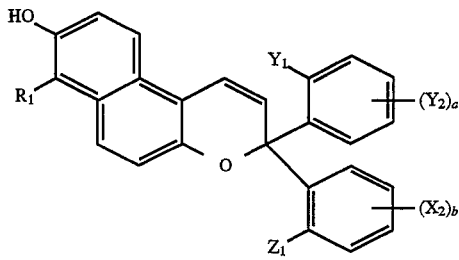

VIII B

Derivatization

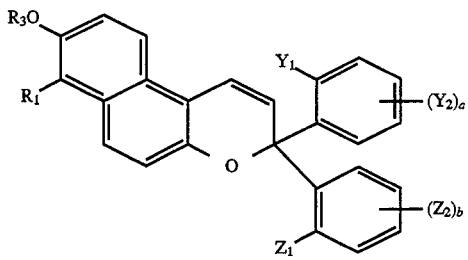

I D

Compounds represented by graphic formulae I A through I D may be used in those applications in which organic photochromic substances may be employed, such as optical lenses, e.g., ophthalmic and plano lenses, face shields, goggles, ski goggles, visors, camera lenses, windows, automotive windshields, aircraft and automotive transparencies, e.g., T-roofs, sidelights and backlights, plastic films and sheets, textiles and coatings, e.g., coating compositions such as paints, and verification marks on security documents, e.g., documents such as banknotes, passports and drivers' licenses for which authentication or verification of authenticity may be desired. Naphthopyrans represented by graphic formula I exhibit color changes from colorless to colors ranging from yellow to orange and red.

Examples of contemplated naphthopyrans within the scope of the invention are the following:

(a) 3,3-diphenyl-8-hydroxy-9-carbopropoxy-3H-naphtho[2,1-b]pyran;

(b) 3-(2-fluorophenyl)-3-(4-methoxyphenyl)-8-hydroxy-9-carbopropoxy-3H-naphtho[2,1-b]pyran;

(c) 3-(2-fluorophenyl)-3-(4-methoxyphenyl)-8-hydroxy-9-carbomethoxy-3H-naphtho[2,1-b]pyran;

(d) 3-(2,4-dimethoxyphenyl)-3-(4-methoxyphenyl)-8-hydroxy-9-carbomethoxy-3H-naphtho{2,1-b]pyran;

(e) 3,3-diphenyl-8-methoxy-9-carbophenoxy-3H-naphtho[2,1-b]pyran;

(f) 3-(2-fluorophenyl)-3-(4-methoxyphenyl)-8-methoxy-9-carbophenoxy-3H-naphtho[2,1-b]pyran;

(g) 3-(2-fluorophenyl)-3-(4-methoxyphenyl)-8-methoxy-9-carbomethoxy-3H-naphtho[2,1-b]pyran;

(h) 3-(2,4-dimethoxyphenyl)-3-(4-methoxyphenyl)-8-acetoxy-9-carbomethoxy-3H-naphtho[2,1-b]pyran;

(i) 3,3-diphenyl-7-methyl-8-methoxy-3H-naphtho[2,1-b]pyran;

(j) 3-(2-methoxy,4-acryloxyphenyl)-3-(4-methacryloxyphenyl)-8-benzyloxy-9-(carbo-1-indolinyl)-3H-naphtho[2,1-b]pyran;

(k) 3-(2,4,6-trifluorophenyl)-3-(2,4,6-trimethoxy-1-naphthyl)-8-acetyl-9-carboniloyl-3H-naphtho[2,1-b]pyran;

(l) 3-(2-fluorophenyl)-3-(3-methoxy-2-thienyl)-7-n-pentyl-8-benzoyloxy-3H-naphtho[2,1-b]pyran; and (m) 3,3-spiro adamantylene-8-acetoxy-9-carbomethoxy-3H-naphtho[2,1-b]pyran;

Commercially available photoreactive inorganic glass lenses containing silver halide particles darken to a neutral gray or brown color in sunlight. In order to duplicate this color change in a plastic lens using the organic photochromic naphthopyrans of the present invention, it is contemplated that such naphthopyrans be used in combination with other appropriate complementary organic photochromic materials so that together they produce the desired gray or brown color shade when the plastic lens containing such photochromic materials is exposed to ultraviolet light. For example, a compound which colors to yellow may be blended with a compound that colors to an appropriate purple to produce a brown shade. Similarly, a compound which is orange in its colored state will produce a shade of gray when used in conjunction with an appropriate blue coloring compound.

Particularly contemplated classes of complementary organic photochromic compounds that may be used in combination with the naphthopyrans of the present invention include: purple/blue spiro(indoline) benzoxazines, such as those described in U.S. Pat. No. 4,816,584; spiro(indoline) pyridobenzoxazine photochromic compounds, such as those described in U.S. Pat. No. 4,637,698; spiro(indoline) naphthoxazines, such as those described in U.S. Pat. Nos. 3,562,172, 3,578,602, 4,215,010 and 4,342,668; and benzopyrans and naphthopyrans other than those of the present invention having a nitrogen-containing substituent on the carbon atom adjacent to the oxygen of the pyran ring, such as those described in U.S. Pat. No. 4,818,096. All of the aforedescribed spirooxazine- and pyran-type organic photochromic compounds are reported to exhibit a color change of from colorless to purple/blue on exposure to ultraviolet light. The disclosures of said U.S. Patents may be incorporated herein by reference.

Other contemplated complementary organic photochromic compounds that are reported to exhibit a color change of from colorless to yellow/orange when exposed to UV light may be used in combination with the naphthopyran compounds of the present invention to augment the yellow/orange color of those activated photochromic compounds. Such complementary yellow/orange compounds include: benzopyrans and naphthopyrans having a spiro adamantylene group in the 2-position of the pyran ring, such as those described in U.S. Pat. No. 4,826,977; and naphthopyran compounds such as those described in U.S. Pat. No. 5,066,818. The disclosures of such U.S. patents also may be incorporated herein by reference.

The naphthopyran compounds of the present invention may be used in admixture with or in conjunction with the aforedescribed complementary or augmenting organic photochromic compounds in amounts and in a ratio such that an organic host material to which the mixture of photochromic compound(s) is applied or in which they are incorporated exhibit a substantially neutral color when activated with unfiltered sunlight, i.e., as near a neutral gray or brown color as possible given the colors of the activated photochromic compounds. The relative amounts of the photochromic compounds used will vary and depend in part upon the relative intensities of the color of the activated species of such compounds.

For example, the naphthopyran compounds of the present invention may be combined with one or more of the aforedescribed purple/blue spirooxazine- and/or pyran-type organic photochromic compounds in amounts and in a ratio such that an organic host material to which the mixture of compounds is applied or in which they are incorporated exhibits a near-brown color. Generally, the weight ratio of each of the aforedescribed spirooxazine- and pyran-type compound(s) to the naphthopyran compound(s) of the present invention will vary from about 1:3 to about 3:1, e.g., between about 1:2 or 0.75:1 and about 2:1.

A near neutral gray color exhibits a spectrum that has relatively equal absorption in the visible range between 400 and 700 nanometers, e.g., between 440 and 660 nanometers. A near neutral brown color exhibits a spectrum in which the absorption in the 400–50 nanometer range is moderately larger than in the 550–700 nanometer range. An alternative way of describing color is in terms of its chromaticity coordinates, which describe the qualities of a color in addition to its luminance factor, i.e., its chromaticity. In the CIE system, the chromaticity coordinates are obtained by taking the ratios of the tristimulus values to their sum, e.g., x=X/X+Y+Z and y=Y/X+Y+Z. Color as described in the CIE system can be plotted on a chromaticity diagram, usually a plot of the chromaticity coordinates x and y. See pages 47–52 of *Principles of Color Technology*, by F. W. Billmeyer, Jr. and Max Saltzman, Second Edition, John Wiley and Sons, N.Y. (1981).

The amount of photochromic substance or composition-containing same applied to or incorporated into a host material is not critical provided that a sufficient amount is used to produce a photochromic effect discernible to the naked eye. Generally such amount can be described as a photochromic amount. The particular amount used depends often upon the intensity of color desired upon irradiation thereof and upon the method used to incorporate or apply the photochromic substances. Typically, the more compound applied or incorporated, the greater is the color intensity.

Generally, the amount of each photochromic substance incorporated into or applied to the host material may range from about 0.01 or 0.05 to about 10 to 20 percent by weight. More typically, the amount of photochromic substance(s) incorporated into or applied to the host material will range from about 0.01 to about 2 weight percent, more particularly, from about 0.01 to about 1 weight percent, e.g., from about 0.1 or 0.5 to about 1 weight percent, based on the weight of the host material. Expressed differently, the total amount of photochromic substance incorporated into or applied to an optical host material may range from about 0.15 to about 0.35 milligrams per square centimeter of surface to which the photochromic substance(s) is incorporated or applied.

Photochromic compounds of the present invention, mixtures of such compounds with other photochromic compounds, or compositions containing same (hereinafter "photochromic substances") may be applied to or incorporated into a host material by various methods described in the art. Such methods include dissolving or dispersing the substance within the host material, e.g., imbibition of the photochromic substance into the host material by immersion of the host material in a hot solution of the photochromic substance or by thermal transfer; providing the photochromic substance as a separate layer between adjacent layers of the host material, e.g., as a part of a polymer film; and applying the photochromic substance as part of a coating placed on the surface of the host material. The term "imbibition" or "imbibe" is intended to mean and include permeation of the photochromic substance alone into the host material, solvent assisted transfer absorption of the photochromic substance into a porous polymer, vapor phase transfer, and other such transfer mechanisms. See U.S. Pat. No. 5,066,818 column 14, line 41 to column 15, line 25 for examples of the above methods.

The polymer host material will usually be transparent, but may be translucent or even opaque. The polymer product need only be transparent to that portion of the electromagnetic spectrum, which activates the photochromic substance, i.e., that wavelength of ultraviolet (UV) light that produces the open form of the substance and that portion of the visible spectrum that includes the absorption maximum wavelength of the substance in its UV activated form, i.e., the open form. Further, the resin color should not be such that it masks the color of the activated form of the photochromic substance, i.e., so the change in color is readily apparent to the observer. Preferably, the host material article is a solid transparent or optically clear material.

Examples of host materials which may be used with the photochromic substances or compositions described herein include: polymers, i.e., homopolymers and copolymers, of polyol(allyl carbonate) monomers, e.g., diethylene glycol bis(allyl carbonate), polymers, i.e., homopolymers and copolymers, of polyfunctional acrylate monomers, polyacrylates, which are polymers of esters of acrylic acid or methacrylic acid, such as methyl acrylate and methyl methacrylate, cellulose acetate, cellulose triacetate, cellulose acetate propionate, cellulose acetate butyrate, poly(vinyl acetate), poly(vinyl alcohol), poly(vinyl chloride), poly(vinylidene chloride), polyurethanes, polycarbonates, poly(ethylene terephthalate), polystyrene, copoly(styrene-methyl methacrylate) copoly(styrene-acrylonitrile), polyvinylbutyral and polymers, i.e., homopolymers and copolymers, of diallylidene pentaerythritol, particularly copolymers with polyol (allyl carbonate) monomers, e.g., diethylene glycol bis(allyl carbonate), and acrylate monomers.

Transparent copolymers and blends of the transparent polymers are also suitable as host materials. Preferably, the host material is an optically clear polymerized organic material prepared from a polycarbonate resin, such as the carbonate-linked resin derived from bisphenol A and phosgene, i.e., poly(4,4'-dioxydiphenol-2,2-propane) carbonate, which is sold under the trademark, LEXAN; a poly(methyl methacrylate), such as the material sold under the trademark, PLEXIGLAS; polymerizates of a polyol(allyl carbonate), especially diethylene glycol bis(allyl carbonate), which monomer is sold under the trademark, CR-39, and polymerizates of copolymers of a polyol (allyl carbonate), e.g., diethylene glycol bis(allyl carbonate), with other copolymerizable monomeric materials, such as copolymers with vinyl acetate, e.g., copolymers of from 80–90 percent diethylene glycol bis(allyl carbonate) and 10–20 percent vinyl acetate, particularly 80–85 percent of the bis(allyl carbonate) and 15–20 percent vinyl acetate, and copolymers with a polyurethane, e.g., a polyesterurethane, having terminal allyl and/or acrylyl functional groups, as described in U.S. Pat. Nos. 4,360,653, 4,994,208, and 5,200,483; cellulose acetate, cellulose propionate, cellulose butyrate, cellulose acetate butyrate, polystyrene and copolymers of styrene with methyl methacrylate, vinyl acetate and acrylonitrile.

Polyol (allyl carbonate) monomers which may be polymerized to form a transparent host material are the allyl carbonates of linear or branched aliphatic or aromatic liquid polyols, e.g., aliphatic glycol bis(allyl carbonate) compounds, or alkylidene bisphenol bis(allyl carbonate) compounds. These monomers can be described as unsaturated polycarbonates of polyols, e.g, glycols. The monomers can be prepared by procedures well known in the art, e.g., U.S. Pat. Nos. 2,370,567 and 2,403,113.

Compatible (chemically and color-wise) tints, i.e., dyes, may be applied to the host material to achieve a more aesthetic result for medical reasons or for reasons of fashion. The particular dye selected will vary and depend on the aforesaid need and result to be achieved. In one embodiment, the dye may be selected to complement the color resulting from the activated photochromic substances, e.g., to achieve a more neutral color or absorb a particular wavelength of incident light. In another embodiment, the dye may be selected to provide a desired hue to the host matrix when the photochromic substance is in an inactivated state.

Typically, tinting is accomplished by immersion of the host material in a heated aqueous dispersion of the selected dye. The degree of tint is controlled by the temperature of the dye bath and the length of time the host material is allowed to remain in the bath. Generally, the dye bath is at temperatures of less than 100° C., e.g., from 70° C. to 90° C., such as 80° C., and the host material remains in the bath for less than five (5) minutes, e.g., between about 0.5 and 3 minutes, e.g., about 2 minutes. The degree of tint is such that the resulting article exhibits from about 70 to 85 percent, e.g., 80–82 percent, light transmission.

Adjuvant materials may also be incorporated into the host material with the photochromic substances prior to, simultaneously with or subsequent to application or incorporation of the photochromic substances in the host material. For example, ultraviolet light absorbers may be admixed with photochromic substances before their application to the host material or such absorbers may be superposed, e.g., superimposed, as a layer between the photochromic substance and the incident light. Further, stabilizers may be admixed with the photochromic substances prior to their application to the host material to improve the light fatigue resistance of the photochromic substances. Stabilizers, such as hindered amine light stabilizers and singlet oxygen quenchers, e.g., a nickel ion complex with an organic ligand, are contemplated. They may be used alone or in combination. Such stabilizers are described in U.S. Pat. No. 4,720,356. Finally, appropriate protective coating(s) may be applied to the surface of the host material. These may be abrasion resistant coatings and/or coatings that serve as oxygen barriers. Such coatings are known in the art.

The present invention is more particularly described in the following examples which are intended as illustrative only, since numerous modifications and variations therein will be apparent to those skilled in the art.

EXAMPLE 1

Step 1

3,7-dihydroxy-2-naphthoic acid (17.4 grams, 0.085 mole) and sodium bicarbonate (21 grams, 0.25 mole) were suspended with stirring in 120 milliliters of dimethylformamide (DMF) in a 500 milliliter round bottom flask equipped with a reflux condenser and nitrogen pad. The mixture was warmed to 70° C. and held there for 2 hours. Afterwards, the mixture was cooled to room temperature and propyl iodide (16.6 grams, 0.1 mole) was added. The stirred reaction mixture was then gradually warmed to 70° C. where it was kept for 3 hours. Subsequently, the contents of the flask were poured into approximately 480 milliliters of ice and water to precipitate the product. The resulting yellow solid was suction filtered and washed with a sodium bicarbonate solution in order to remove any unreacted starting material. The yellow solid was next washed with water and air dried. High-performance liquid chromatographic (HPLC) analysis revealed that the solid consisted of propyl 3,7-dihydroxy-2-naphthoate containing a small amount of propyl 3-hydroxy-2-naphthoate. The yield of 3,7-dihydroxy-2-naphthoate was 16.7 grams.

Step 2

Propyl 3,7-dihydroxy-2-naphthoate (3.0 grams, 0.012 mole) from Step 1 was added to a reaction flask containing 0.015 mole 1,1-diphenyl-2-propyn-1-ol in 100 milliliters of toluene and stirred at room temperature. A catalytic amount of dodecylbenzene sulfonic acid (an amount sufficient to produce a deep red-brown colored solution) was added and the reaction mixture was heated for five hours at 50° C. Afterwards, the reaction mixture was kept at room temperature for about 18 hours and then washed twice with water. Toluene was removed under vacuum to yield an oily product. The resultant oil was taken up in 5 to 10 milliliters of a 2:1 mixture of hexane:ethyl acetate. Crystals of the product formed and were suction filtered and washed with fresh solvent until no additional color was removed. Occasionally, if the oil solvent mixture did not crystallize, the mixture was purified on a silica gel column using a hexane:ethyl acetate mixture as eluant. The photochromic fractions were combined and the remaining eluant was removed under vacuum. The resulting residue was triturated in hexane, suction filtered and dried. A nuclear magnetic resonance (NMR) spectrum showed the recovered product, 2.4 grams, to have a structure consistent with 3,3-diphenyl-8-hydroxy-9-carbopropoxy-3H-naphtho[2,1-b]pyran.

EXAMPLE 2

The procedure of Example 1 was followed except that 1-(2-fluorophenyl)-1-(4-methoxyphenyl)-2-propyn-1-ol was used in place of 1,1-diphenyl-2-propyn-1-ol in Step 2. A nuclear magnetic resonance (NMR) spectrum showed the recovered product, 5.0 grams, to have a structure consistent with 3-(2-fluorophenyl)-3-(4-methoxyphenyl)-8-hydroxy-9-carbopropoxy-3H-naphtho[2,1-b]pyran.

EXAMPLE 3

The procedure of Example 1 was followed except that methyl iodide was used in place of propyl iodide in Step 1 and 1-(2-fluorophenyl)-1-(4-methoxyphenyl)-2-propyn-1-ol was used in place of 1,1-diphenyl-2-propyn-1-ol in Step 2. The recovered product, 3.0 grams, had a melting point of 104° to 106° C. A nuclear magnetic resonance (NMR) spectrum showed the recovered product to have a structure consistent with 3-(2-fluorophenyl)-3-(4-methoxyphenyl)-8-hydroxy-9-carbomethoxy-3H-naphtho[2,1-b]pyran.

EXAMPLE 4

The procedure of Example 3 was followed except that 1-(2,4-dimethoxyphenyl)-1-(4-methoxyphenyl)-2-propyn-1-ol was used in place of 1-(2-fluorophenyl)-1-(4-methoxyphenyl)-2-propyn-1-ol in Step 2. The recovered product, 3.0 grams, had a melting point of 128° to 130° C. A nuclear magnetic resonance (NMR) spectrum showed the recovered product to have a structure consistent with 3-(2,4-dimethoxyphenyl)-3-(4-methoxyphenyl)-8-hydroxy-9-carbomethoxy-3H-naphtho[2,1-b]pyran.

EXAMPLE 5

Two grams of 3,3-diphenyl-8-hydroxy-9-carbopropoxy-3H-naphtho[2,1-b]pyran from Example 1 was added to a reaction flask containing 100 milliliters of acetone. Two grams each of anhydrous potassium carbonate and dimethyl sulfate were added to the reaction flask. The resulting reaction mixture was stirred and heated for 20 hours at 50° C. under a nitrogen atmosphere. After cooling to room temperature, acetone was removed under vacuum. 25 milliliters each of water and methylene chloride were added to the mixture, which was then stirred for 15 minutes. The organic phase was separated and the residual methylene chloride was removed under vacuum. The resulting oil was crystallized from hexane. Crystals of the product were suctioned filtered, triturated with fresh hexane, suction filtered and dried. The recovered product, 1.3 grams, had a melting point of 127° to 129° C. A nuclear magnetic resonance (NMR) spectrum showed the recovered product to have a structure consistent with 3,3-diphenyl-8-methoxy-9-carbopropoxy-3H-naphtho[2,1-b]pyran.

EXAMPLE 6

The procedure of Example 5 was followed except that 3-(2-fluorophenyl)-3-(4-methoxyphenyl)-8-hydroxy-9-carbopropoxy-3H-naphtho[2,1-b]-pyran from Example 2 was used in place of 3,3-diphenyl-8-hydroxy-9-carbopropoxy-3H-naphtho[2,1-b]-pyran. The recovered product, 0.8 grams, had a melting point of 103° to 105° C. A nuclear magnetic resonance (NMR) spectrum showed the recovered product to have a structure consistent with 3-(2-fluoro-phenyl)-3-(4-methoxyphenyl)-8-methoxy-9-carbopropoxy-3H-naphtho[2,1-b]pyran.

EXAMPLE 7

The procedure of Example 5 was followed except that 3-(2-fluorophenyl)-3-(4-methoxyphenyl)-8-hydroxy-9-carbomethoxy-3H-naphtho[2,1-b]-pyran from Example 3 was used in place of 3,3-diphenyl- 8-hydroxy-9-carbopropoxy-3H-naphtho[2,1-b]-pyran. The recovered product, 1.2 grams, had a melting point of 174° to 176° C. A nuclear magnetic resonance (NMR) spectrum showed the recovered product to have a structure consistent with 3-(2-fluorophenyl)-3-(4-methoxyphenyl)-8-methoxy-9-carbomethoxy-3H-naphtho[2,1-b]pyran.

EXAMPLE 8

Three grams of 3-(2,4-dimethoxyphenyl)-3-(4-methoxyphenyl)-8-hydroxy-9-carbomethoxy-3H-naphtho[2,1-b]-pyran prepared in Example 4 was added to a reaction flask containing 1.5 grams each of acetic anhydride and triethyl amine in 100 milliliters of chloroform. The mixture was refluxed under a nitrogen atmosphere for 24 hours. The resulting mixture was poured into 50 milliliters of dilute hydrochloric acid, the organic layer was separated, and the solvent, chloroform, was removed under vacuum. About 5 to 10 milliliters of a mixture of hexane:ethyl acetate was added to crystallize the product from the resulting residue. Crystals of the product were suction filtered, washed with fresh solvent until no additional color was removed, and then dried. The recovered product, 1.8 grams, had a melting point of 168° to 169° C. A nuclear magnetic resonance (NMR) spectrum showed the recovered product to have a structure consistent with 3-(2,4-dimethoxy-phenyl)-3-(4-methoxyphenyl)-8-acetoxy-9-carbomethoxy-3H-naphtho-[2,1-b]pyran.

EXAMPLE 9

Step 1

Ten grams of purchased 5-methyl-6-methoxy-2-bromonaphthalene was added to the reaction vessel of a 500 milliliter autoclave, containing 150 milliliters of an aqueous solution of potassium hydroxide (15 grams), 30 grams of polyethylene glycol monomethyl ether, and one gram of a 50:50 mixture of copper bronze and copper powder. The autoclave was sealed and heated to 200° C. while stirring at 1200 revolutions per minute (RPM). After five hours, the autoclave was cooled to room temperature and the contents were filtered. The aqueous filtrate was acidified with dilute hydrochloric acid and the resulting precipitate was suction filtered. The recovered solid was dissolved in aqueous sodium hydroxide and the solution filtered. The resulting filtrate was acidified with dilute hydrochloric acid and the resulting precipitate suction filtered and dried. The recovered product, 5.5 grams, had a melting point of 122° to 124° C. A nuclear magnetic resonance (NMR) spectrum showed the recovered product to have a structure consistent with 5-methyl-6-methoxy-2-naphthol.

Step 2

Two grams of 5-methyl-6-methoxy-2-naphthol, prepared in Step 1, was added to a reaction flask containing a molar excess of 1,1-diphenyl-2-propyn-1-ol in 150 milliliters of toluene. A catalytic amount of dodecylbenzene sulfonic acid (an amount sufficient to produce a dark red-brown colored solution) was added and the reaction mixture was heated for three hours at 45° C. Afterwards, 100 milliliters of water was added and the organic layer was separated. The organic layer was first washed with dilute aqueous sodium hydroxide and then washed with water. Toluene was removed under vacuum yielding a pasty solid. The pasty solid was slurried with a few milliliters of diethyl ether and filtered. The resulting crystals were washed with diethyl ether until no additional color was removed and then dried. The recovered product, 1.4 grams, had a melting point of 230° to 231.5° C.

A nuclear magnetic resonance (NMR) spectrum showed the recovered product to have a structure consistent with 3,3-diphenyl-7-methyl-8-methoxy-3H-naphtho[2,1-b]pyran.

COMPARATIVE EXAMPLE 1

Step 1

A reaction flask was charged with 200 milliliters of acetone, powdered potassium carbonate (13.8 grams, 0.1 mole) and 2,6-dihydroxynaphthalene (16.0 grams, 0.1 mole). Dimethylsulfate (12.6 grams, 0.1 mole) was added dropwise and the reaction mixture was stirred at room temperature for 72 hours under a nitrogen atmosphere. Sodium hydroxide (200 milliliters of a 10% aqueous solution) was then added to the reaction flask. The white precipitate that formed was removed by vacuum filtration. The aqueous filtrate was acidified with hydrochloric acid to a pH of 3 and the aqueous solution extracted three times with 100 milliliter portions of methylene chloride. The extracts were combined, dried over anhydrous magnesium sulfate for 10 minutes and the solvent removed under vacuum. The residue was washed with hot water and dried to yield 3.0 grams of a solid product, which was confirmed by NMR spectroscopy to be 6-methoxy-2-hydroxynaphthalene.

Step 2

6-methoxy-2-hydroxynaphthalene (1.1 grams, 0.006 mole) from Step 1, was added to a reaction flask containing 100 milliliters of benzene and 1,1-diphenyl-2-propyn-1-ol (1.3 grams, 0.006 mole). A catalytic amount (approximately 20 milligrams) of p-toluene sulfonic acid was added and the resulting mixture stirred under a nitrogen atmosphere. The reaction mixture was heated gently at 50° C. for 4 hours, cooled, and then 200 ml of a 10% aqueous sodium hydroxide solution was added. After stirring for 15 minutes, the reaction mixture was extracted twice with 100 milliliter portions of methylene chloride. The extracts were combined, dried over anhydrous magnesium sulfate and the solvent removed under vacuum. The product (1.0 grams) melted at 173°–175° C. An NMR spectrum showed the recovered product to have a structure consistent with 3,3-diphenyl-8-methoxy-3H-naphtho [2,1-b]pyran.

COMPARATIVE EXAMPLE 2

1,1-diphenyl-2-propyn-1-ol (20.8 grams, 0.1 mole) was added to a reaction flask containing 200 milliliters of benzene and 15 grams of 2-naphthol. The reaction mixture was warmed to 55° C. and after all of the 2-naphthol was dissolved, 0.25 grams of p-toluenesulfonic acid was added. The mixture changed from light tan to dark black and the temperature rose to 70° C. After a few minutes, the reaction mixture lightened and began to cool. Thirty minutes later, the contents of the flask were poured into 100 milliliters of 10 percent aqueous sodium hydroxide and shaken. The organic phase was separated, washed once with 10 percent aqueous sodium hydroxide, and then washed with water. Benzene was removed on a rotary evaporator and the resulting light tan solid residue was slurried with 100 milliliters of hexane and then filtered. The filtered solid was washed again with 100 milliliters of hexane and dried to provide 18.4 grams of the product, 3,3-diphenyl-3H-naphtho [2,1-b]pyran. The solid product had a melting point of 156°–158° C. and was 98 percent pure, as determined by liquid chromatographic analysis.

COMPARATIVE EXAMPLE 3

Step 1

A reaction flask was charged with eight grams of 2-fluoro-4'-methoxybenzophenone, (prepared by the Friedel-Crafts reaction of 2-fluorobenzoylchloride with anisole), 150 milliliters of tetrahydrofuran, and 14.0 grams of an 18 weight percent slurry of sodium acetylide in xylene/mineral oil. The reaction mixture was stirred at room temperature under a nitrogen atmosphere for 72 hours. The contents of the flask were poured into a 500 milliliter beaker containing ice water and extracted three times with 100 milliliter portions of methylene chloride. The extracts were combined, dried over anhydrous magnesium sulfate and the solvent removed under vacuum. The crude product, 7.0 grams, was isolated as a yellow oil. This oil was shown by NMR to contain the desired product; 1-(2-fluorophenyl)-1-(4-methoxyphenyl)-2-propyn-1-ol.

Step 2

1-(2-fluorophenyl)-1-(4-methoxyphenyl)-2-propyn-1-ol (2.4 grams, 0.008 mole), as prepared in Step 1, was added to a reaction flask containing 100 milliliters of benzene and 6-methoxy-2-hydroxynaphthalene (1.4 grams, 0.008 mole). A catalytic amount of p-toluene sulfonic acid (approximately 20 milligrams) was added and the resulting mixture stirred and heated between 30°–35° C. under a nitrogen atmosphere for 3 hours. The reaction mixture was poured into an equal volume of 20% aqueous sodium hydroxide and extracted three times with 100 milliliter portions of methylene chloride. The extracts were combined, dried over anhydrous magnesium sulfate and solvent removed under vacuum. The resultant oil was column chromatographed on silica using 1:10 mixture of ethyl acetate-:hexane as the eluant. The photochromic fractions were combined, concentrated under vacuum, and crystallized by cooling in diethyl ether. The crystals (0.5 g) were suction filtered and dried. The melting point of the crystals was 120°–123° C. An NMR spectrum showed the recovered product to have a structure consistent with 3-(2-fluorophenyl)-3-(4-methoxyphenyl)-8-methoxy-3H-naphtho[2,1-b]pyran.

COMPARATIVE EXAMPLE 4

Step 1

1,3-Dimethoxybenzene (13.8 grams, 0.1 mole) and p-anisoyl chloride (17 grams, 0.1 mole) were dissolved in 200 milliliters of methylene chloride and stirred at room temperature. Anhydrous aluminum chloride (15 grams) was added slowly to the reaction mixture over a period of 15 minutes with stirring. After stirring an additional 15 minutes, the contents of the flask were carefully poured into 200 milliliters of a mixture of ice and dilute hydrochloric acid. The organic fraction was separated and washed with water. The solvent was removed on a rotary evaporator leaving an oily product that solidified on standing. This solid was broken-up, washed with two 50 milliliter portions of pentane, and dried, yielding 2,4,4'-trimethoxybenzophenone.

Step 2

10 grams of 2,4,4'-trimethoxybenzophenone, as prepared in Step 1, was converted to the corresponding propargyl alcohol by the procedure described in Step 1 of Comparative Example 3. The resulting crude product was shown by NMR to contain the desired product 1-(2,4-dimethoxyphenyl)-1-(4-methoxyphenyl)-2-propyn-1-ol.

Step 3

The crude propargyl alcohol from step 2 was added to a reaction flask containing a slurry of 5 grams of 2-naphthol in 200 milliliters of toluene. A few drops of dodecyl benzene sulfonic acid (an amount sufficient to turn the mixture a dark red-brown color) were added and the mixture was warmed to 50° C. for a period of two hours. The reaction mixture was cooled and washed twice with 50 milliliter portions of water. The organic fraction was concentrated on a rotary evaporator and the residue chromatographed on a silica column and eluted with a 2:1 mixture of hexane:ethyl acetate. The photochromic fractions were combined and concentrated under vacuum. The residue was induced to crystallize by adding a few milliliters (less than 10 milliliters) of a hexane diethyl ether mixture and cooling. The product crystals were washed with diethyl ether and dried to yield 4 grams of a product having a melting point of 144°–146° C. A nuclear magnetic resonance (NMR) spectrum showed the solid product to have a structure consistent with 3-(2,4-dimethoxyphenyl)-3-(4-methoxyphenyl)-3H-naphtho[2,1-b]pyran.

EXAMPLE 10

Part A

The products of Examples 1, 5, 8, 9, and Comparative Examples 1 and 2 were dissolved in diethylene glycol dimethyl ether. The concentrations of the resulting solutions were approximately 0.5 milligram per milliliter. Each solution was tested in a UV spectrophotometer to determine its activating wavelength. The activating wavelength reported in Table 1 is the wavelength at which activation of the photochromic compound occurs in diethylene glycol dimethyl ether. That value corresponds to the absorption peak in the ultraviolet region that is closest to the visible region or the threshold range, i.e., 390 to 410 nanometers, if there is only one absorption peak in this region. If there is more than one absorption peak, the activating wavelength corresponds most closely to the absorption peak that immediately proceeds the peak of longer wavelength in the ultraviolet region or the threshold range.

Part B

Further testing was done on naphthopyrans of Example 5 and Comparative Examples 1 and 2, which were imbibed by thermal transfer into test squares of a homopolymer of diethylene glycol bis(allyl carbonate) by the following procedure. Each naphthopyran was dissolved into toluene solvent to form a 4 weight percent solution of the compound. A piece of No. 4 Whatman filter paper was saturated with the naphthopyran solution and allowed to air dry. The dried filter paper was placed on one side of the polymer test square, which measured ⅛ inch (0.3 centimeter)×2 inch (5.1 centimeters)×2 inch (5.1 centimeters). A piece of untreated filter paper was placed on the other side of the polymer test square and the resulting sandwich placed between two plates of flat aluminum metal plates. The entire assembly was then placed in a 155° C. oven for a time sufficient to thermally transfer the naphthopyran into the polymer test square. Residence times in the oven were adjusted to imbibe comparable amounts of the naphthopyran compounds in order to yield a comparable UV absorbance at their activating wavelength. The imbibed test squares were washed with acetone after removal from the oven.

The test samples were evaluated for photochromic response rates on an optical bench. The samples were illuminated by a 150 watt Xenon lamp fitted with a copper sulfate bath, a 320 nanometer filter, and a neutral density filter at an intensity of about one sun. A second beam of light provided by a filtered tungsten lamp arranged to pass through the sample area exposed by the UV source was used to monitor changes in transmission of the sample over different wavelength ranges in the visible region of the spectrum. The intensity of the monitoring beam after passing through the sample was measured by means of an IL-1500 radiometer equipped with a silicon detector head and matching filters.

The $\Delta$ OD/Min, which represents the sensitivity of the photochromic compound's response to UV light, was measured using photopic filters on the silicon detector. The response of the filtered detector approximated the luminosity curve. The $\Delta$ OD was measured over the first five (5) seconds of UV exposure, then expressed on a per minute basis. The saturation optical density (OD) was taken under identical conditions as the $\Delta$ OD/Min, except UV exposure was continued for 20 minutes for the examples in Table 2. The Bleach Rate T ½ is the time interval in seconds for the absorbance of the activated form of the naphthopyran in the test polymers to reach one half the highest absorbance at room temperature (72° F., 22.2° C.) after removal of the source of activating light. Results are tabulated in Table 2.

Part C

The solar response for naphthopyrans of Example 7 and Comparative Examples 3 and 4 was measured using the optical bench described in Part B. The naphthopyrans were imbibed by thermal transfer into test squares of a polymeric matrix prepared from a diethylene glycol bis(allyl carbonate) composition and two optical density measurements were made after 15 minute exposures to a UV source first fitted with a 320 nanometer filter and then fitted with a 360 nanometer filter. The loss in response was calculated by subtracting the optical density obtained with the 360 nanometer filter from the optical density obtained with the 320 nanometer filter and then dividing this figure by the optical density obtained with the 320 nanometer filter and multiplying by 100.

The loss in response measurement, expressed as a percent, simulates the difference between the photochromic response of the compounds exposed to full mid-day sun and to low light conditions, such as early day and late in the day when the lower wavelength components of the UV spectrum are attenuated. The results for the loss in response, activating wavelength, and the Bleach Rate T ½ are listed in Table 3.

TABLE 1

| Activating Wavelength in Diethylene Glycol Dimethyl Ether | |
|---|---|
| | ACTIVATING WAVELENGTH |
| COMPOUND EXAMPLE | |
| 1 | 408 |
| 5 | 382 |
| 8 | 376 |
| 9 | 369 |
| COMPARATIVE EXAMPLE | |
| 1 | 359 |
| 2 | 348 |

TABLE 2

| | Δ OD/Min SENSITIVITY | Δ OD @ SATURATION | BLEACH RATE T 1/2 (SEC.) |
|---|---|---|---|
| COMPOUND EXAMPLE | | | |
| 5 | 1.4 | 0.55 | 80 |
| COMPARATIVE EXAMPLE | | | |
| 1 | 1.25 | 0.73 | 87 |
| 2 | 0.87 | 0.36 | 45 |

TABLE 3

| | Δ OD @ 320 nm | Δ OD @ 360 nm | % LOSS IN RESPONSE | ACTIVATING WAVELENGTH | BLEACH RATE T 1/2 (SEC.) |
|---|---|---|---|---|---|
| COMPOUND EXAMPLE | | | | | |
| 7 | 0.187 | 0.184 | 2% | 384 | 196 |
| COMPARATIVE EXAMPLE | | | | | |
| 3 | 0.266 | 0.249 | 6% | 359 | 356 |
| 4 | 0.260 | 0.196 | 25% | 348 | 338 |

The results in Table 1 demonstrate the unexpectedly higher activating wavelength of the compounds of the present inventions, vis-a-vis, comparative example 1, which has a methoxy substituent at the number 8 carbon atom, and comparative example 2, which has no substituents on the naphthalene nucleus. Table 2 shows that the compound of example 5 has an increased sensitivity as compared to the compounds of comparative examples 1 and 2. The results in Table 3 reveal less reduction in optical density measured after exposure to a xenon light with a 360 nm cutoff filter as compared to the optical density measured after exposure to the same light source and a 320 nm cutoff filter, for compound example 7 as compared to comparative examples 3 and 4. Also, Table 3 shows that the compound of example 7 has a more acceptable Bleach Rate T ½, i.e., rate of fade.

Although the present invention has been described with reference to the specific details of particular embodiments thereof, it is not intended that such details be regarded as limitations upon the scope of the invention except insofar as and to the extent that they are included in the accompanying claims.

What is claimed is:

1. A naphthopyran compound represented by the following graphic formula:

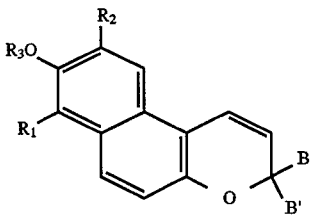

wherein:

(a) $R_1$ is hydrogen or a $C_1-C_6$ alkyl; $R_2$ is hydrogen or the group, —C(O)W, W being —OR$_4$ or —N(R$_5$)R$_6$, wherein $R_4$ is hydrogen, allyl, $C_1-C_6$ alkyl, phenyl, $C_1-C_6$ monoalkyl substituted phenyl, $C_1-C_6$ monoalkoxy substituted phenyl, phenyl($C_1-C_3$)alkyl, $C_1-C_6$ monoalkyl substituted phenyl($C_1-C_3$)alkyl, $C_1-C_6$ monoalkoxy substituted phenyl($C_1-C_3$)alkyl, $C_1-C_6$ alkoxy($C_2-C_4$)alkyl, or $C_1-C_6$ monohaloalkyl, and wherein $R_5$ and $R_6$ are each selected from the group consisting of hydrogen, $C_1-C_6$ alkyl, $C_5-C_7$ cycloalkyl, phenyl and mono- or di-substituted phenyl, or $R_5$ and $R_6$ together with the nitrogen form a mono- or di-substituted or unsubstituted heterocyclic ring selected from the group consisting of indolinyl, morpholino, piperidino, 1-pyrrolidyl, 1-pyrrolinyl, 1-imidazolidyl, 2-imidazolin-1-yl, 2-pyrazolidyl and 1-piperazinyl, said phenyl and heterocyclic ring substituents being selected from $C_1-C_6$ alkyl and $C_1-C_6$ alkoxy and said halo substituent being chloro or fluoro; $R_3$ is hydrogen, $C_1-C_6$ alkyl, phenyl($C_1-C_3$)alkyl, $C_1-C_6$ monoalkyl substituted phenyl($C_1-C_3$)alkyl, $C_1-C_6$ monoalkoxy substituted phenyl($C_1-C_3$)alkyl, $C_1-C_6$ alkoxy($C_2-C_4$)alkyl, $C_5-C_7$ cycloalkyl, $C_1-C_4$ monoalkyl substituted $C_5-C_7$ cycloalkyl, $C_1-C_6$ monohaloalkyl, allyl or the group, —C(O)X, wherein X is a $C_1-C_6$ alkyl, phenyl, $C_1-C_6$ mono-or $C_1-C_6$ di-alkyl substituted phenyl, $C_1-C_6$ mono- or $C_1-C_6$ di-alkoxy substituted phenyl, $C_1-C_6$ alkoxy, phenoxy, $C_1-C_6$ mono- or $C_1-C_6$ di-alkyl substituted phenoxy, $C_1-C_6$ mono- or $C_1-C_6$ di-alkoxy substituted phenoxy, $C_1-C_6$ alkylamino, phenylamino, $C_1-C_6$ mono- or $C_1-C_6$ di-alkyl substituted phenylamino, or $C_1-C_6$ mono- or $C_1-C_6$ di-alkoxy substituted phenylamino, and said halo substituent being chloro, fluoro or bromo, provided that one of $R_1$ or $R_2$ is hydrogen;

(b) B is selected from the group consisting of the substituted or unsubstituted aryl groups phenyl and naphthyl, and (c) B' is selected from the group consisting of the substituted or unsubstituted heterocyclic aromatic groups pyridyl, furyl, benzofuryl, thienyl, and benzothienyl, said aryl and heterocyclic substituents being selected from the group consisting of hydroxy, $C_1-C_5$ alkyl, $C_1-C_5$ haloalkyl, $C_1$–$C_5$ alkoxy, $C_1$–$C_5$ alkoxy($C_1$–$C_4$)alkyl, $C_1$–$C_5$ dialkylamino, acryloxy, methacryloxy, and halogen, said halogen or (halo) groups being fluoro, chloro, or bromo.

2. The naphthopyran of claim 1 wherein B is a phenyl group; represented respectively by the following graphic formulae:

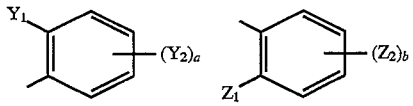

wherein, $Y_1$ is selected from the group consisting of $C_1$–$C_5$ alkyl, $C_1$–$C_5$ alkoxy, fluoro, and chloro, $Z_1$ is selected from the group consisting of hydrogen and $Y_1$, each $Y_2$ and $Z_2$ are selected from the group consisting of $C_1$–$C_5$ alkyl, $C_1$–$C_5$ alkoxy, hydroxy, halogen, acryloxy, and methacryloxy, and a and b are each integers of from 0 to 2.

3. The naphthopyran of claim 2 wherein $R_1$ is hydrogen or methyl; $R_2$ is hydrogen or the group, —C(O)W, W being —$OR_4$, wherein $R_4$ is $C_1$–$C_3$ alkyl or allyl; and $R_3$ is hydrogen, $C_1$–$C_3$ alkyl, phenyl($C_1$–$C_3$)alkyl, or the group, —C(O)X wherein X is a $C_1$–$C_4$ alkyl.

4. The naphthopyran of claim 3 wherein $Y_1$ is $C_1$–$C_3$ alkyl, $C_1$–$C_3$ alkoxy, or fluoro, $Z_1$ is a hydrogen, each $Y_2$ and $Z_2$ is selected from the group consisting of $C_1$–$C_3$ alkyl and $C_1$–$C_3$ alkoxy, a is the integer 0 or 1, and b is an integer from 0 to 2.

5. A photochromic article comprising an organic host material and a photochromic amount of a naphthopyran compound represented by the following graphic formula:

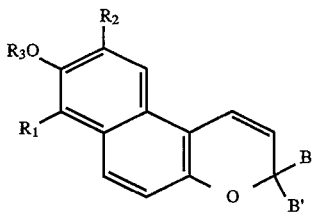

wherein:
(a) $R_1$ is hydrogen or a $C_1$–$C_6$ alkyl; $R_2$ is hydrogen or the group, —C(O)W, W being —$OR_4$ or —N($R_5$)$R_6$, wherein $R_4$ is hydrogen, allyl, $C_1$–$C_6$ alkyl, phenyl, $C_1$–$C_6$ monoalkyl substituted phenyl, $C_1$–$C_6$ monoalkoxy substituted phenyl, phenyl($C_1$–$C_3$)alkyl, $C_1$–$C_6$ monoalkyl substituted phenyl($C_1$–$C_3$)alkyl, $C_1$–$C_6$ monoalkoxy substituted phenyl($C_1$–$C_3$)alkyl, $C_1$–$C_6$ alkoxy($C_2$–$C_4$)alkyl, or $C_1$–$C_6$ monohaloalkyl, and wherein $R_5$ and $R_6$ are each selected from the group consisting of hydrogen, $C_1$–$C_6$ alkyl, $C_5$–$C_7$ cycloalkyl, phenyl and mono- or di-substituted phenyl, or $R_5$ and $R_6$ together with the nitrogen form a mono- or di-substituted or unsubstituted heterocyclic ring selected from the group consisting of indolinyl, morpholino, piperidino, 1-pyrrolidyl, 1-pyrrolinyl, 1-imidazolidyl, 2-imidazolin-1-yl, 2-pyrazolidyl and 1-piperazinyl, said phenyl and heterocyclic ring substituents being selected from $C_1$–$C_6$ alkyl and $C_1$–$C_6$ alkoxy and said halo substituent being chloro or fluoro; $R_3$ is hydrogen, $C_1$–$C_6$ alkyl, phenyl($C_1$–$C_3$)alkyl, $C_1$–$C_6$ monoalkyl substituted phenyl($C_1$–$C_3$)alkyl, $C_1$–$C_6$ monoalkoxy substituted phenyl($C_1$–$C_3$)alkyl, $C_1$–$C_6$ alkoxy($C_2$–$C_4$)alkyl, $C_5$–$C_7$ cycloalkyl, $C_1$–$C_4$ monoalkyl substituted $C_5$–$C_7$ cycloalkyl, $C_1$–$C_6$ monohaloalkyl, allyl or the group, —C(O)X, wherein X is a $C_1$–$C_6$ alkyl, phenyl, $C_1$–$C_6$ mono-or $C_1$–$C_6$ di-alkyl substituted phenyl, $C_1$–$C_6$ mono- or $C_1$–$C_6$ di-alkoxy substituted phenyl, $C_1$–$C_6$ alkoxy, phenoxy, $C_1$–$C_6$ mono- or $C_1$–$C_6$ di-alkyl substituted phenoxy, $C_1$–$C_6$ mono- or $C_1$–$C_6$ di-alkoxy substituted phenoxy, $C_1$–$C_6$ alkylamino, phenylamino, $C_1$–$C_6$ mono- or $C_1$–$C_6$ di-alkyl substituted phenylamino, or $C_1$–$C_6$ mono- or $C_1$–$C_6$ di-alkoxy substituted phenylamino, and said halo substituent being chloro, fluoro or bromo, provided that one of $R_1$ or $R_2$ is hydrogen; and (b) B is selected from the group consisting of the substituted or unsubstituted aryl groups phenyl and naphthyl, and (c) B' is selected from the group consisting of the substituted or unsubstituted heterocyclic aromatic groups pyridyl, furyl, benzofuryl, thienyl, and benzothienyl, said aryl and heterocyclic substituents being selected from the group consisting of hydroxy, $C_1$–$C_5$ alkyl, $C_1$–$C_5$ haloalkyl, $C_1$–$C_5$ alkoxy, $C_1$–$C_5$ alkoxy($C_1$–$C_4$)alkyl, $C_1$–$C_5$ dialkylamino, acryloxy, methacryloxy, and halogen, said halogen or (halo) groups being fluoro, chloro, or bromo.

6. The photochromic article of claim 5 wherein the organic host material is selected from the group consisting of polyacrylates, cellulose acetate, cellulose triacetate, cellulose acetate propionate, cellulose acetate butyrate, poly (vinyl acetate), poly(vinyl alcohol), poly(vinyl chloride), poly(vinylidene chloride), polycarbonate, polyurethanes, poly(ethylene terephthalate), polystyrene, copoly(styrene-methylmethacrylate), copoly(styrene-acrylonitrile, polyvinylbutyral and polymers of members of the group consisting of polyol(allyl carbonate) monomers, polyfunctional acrylate monomers, and diallylidene pentaerythritol monomers.

7. The photochromic article of claim 6 wherein B is a phenyl group; represented respectively by the following graphic formulae:

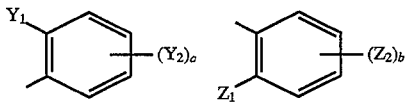

wherein, $Y_1$ is selected from the group consisting of $C_1$–$C_5$ alkyl, $C_1$–$C_5$ alkoxy, fluoro, and chloro, $Z_1$ is selected from the group consisting of hydrogen and $Y_1$, each $Y_2$ and $Z_2$ are selected from the group consisting of $C_1$–$C_5$ alkyl, $C_1$–$C_5$ alkoxy, hydroxy, halogen, acryloxy, and methacryloxy, and a and b are each integers from 0 to 2.

8. The photochromic article of claim 7 wherein $R_1$ is hydrogen or methyl; $R_2$ is hydrogen or the group, —C(O)W, W being —$OR_4$, wherein $R_4$ is $C_1$–$C_3$ alkyl or allyl; and $R_3$ is hydrogen, $C_1$–$C_3$ alkyl, phenyl($C_1$–$C_3$)alkyl, or the group, —C(O)X wherein X is a $C_1$–$C_4$ alkyl.

9. The photochromic article of claim 8 wherein $Y_1$ is $C_1$–$C_3$ alkyl, $C_1$–$C_3$ alkoxy, or fluoro, $Z_1$ is a hydrogen, each $Y_2$ and $Z_2$ is selected from the group consisting of $C_1$–$C_3$ alkyl and $C_1$–$C_3$ alkoxy, a is the integer 0 or 1, and b is an integer from 0 to 2.

10. The photochromic article of claim 9 wherein the organic host material is a solid transparent homopolymer or copolymer of diethylene glycol bis(allyl carbonate), poly(4, 4'dioxydiphenol-2,2-propane) carbonate, poly(methylmethacrylate), polyvinylbutyral or a polyurethane.

11. The photochromic article of claim 10 wherein the photochromic compound is present in an amount of from about 0.15 to 0.35 milligrams per square centimeter of organic host material surface to which the photochromic compound is incorporated or applied.

12. The photochromic article of claim 11 wherein the article is a lens.

13. A photochromic article comprising a solid transparent polymerized organic host material and a photochromic amount of each of (a) a first photochromic substance selected from the group consisting of spiro(indoline) naphthoxazines, spiro(indoline) pyridobenzoxazines, spiro(indoline) benzoxazines, and benzopyrans or naphthopyrans other than the photochromic substance of (b) having a nitrogen-containing substituent on the carbon atom adjacent to the oxygen of the pyran ring, and (b) a second photochromic substance selected from naphthopyran compounds represented by the following graphic formula:

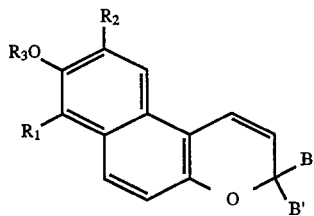

wherein:

(a) $R_1$ is hydrogen or a $C_1$–$C_6$ alkyl; $R_2$ is hydrogen or the group, —C(O)W, W being —$OR_4$ or —$N(R_5)R_6$, wherein $R_4$ is hydrogen, allyl, $C_1$–$C_6$ alkyl, phenyl, $C_1$–$C_6$ monoalkyl substituted phenyl, $C_1$–$C_6$ monoalkoxy substituted phenyl, phenyl($C_1$–$C_3$)alkyl, $C_1$–$C_6$ monoalkyl substituted phenyl($C_1$–$C_3$)alkyl, $C_1$–$C_6$ monoalkoxy substituted phenyl($C_1$–$C_3$)alkyl, $C_1$–$C_6$ alkoxy($C_2$–$C_4$)alkyl, or $C_1$–$C_6$ monohaloalkyl, and wherein $R_5$ and $R_6$ are each selected from the group consisting of hydrogen, $C_1$–$C_6$ alkyl, $C_5$–$C_7$ cycloalkyl, phenyl and mono- or di-substituted phenyl, or $R_5$ and $R_6$ together with the nitrogen form a mono- or di-substituted or unsubstituted heterocyclic ring selected from the group consisting of indolinyl, morpholino, piperidino, 1-pyrrolidyl, 1-pyrrolinyl, 1-imidazolidyl, 2-imidazolin-1-yl, 2-pyrazolidyl and 1-piperazinyl, said phenyl and heterocyclic ring substituents being selected from $C_1$–$C_6$ alkyl and $C_1$–$C_6$ alkoxy and said halo substituent being chloro or fluoro; $R_3$ is hydrogen, $C_1$–$C_6$ alkyl, phenyl($C_1$–$C_3$)alkyl, $C_1$–$C_6$ monoalkyl substituted phenyl($C_1$–$C_3$)alkyl, $C_1$–$C_6$ monoalkoxy substituted phenyl($C_1$–$C_3$)alkyl, $C_1$–$C_6$ alkoxy($C_2$–$C_4$)alkyl, $C_5$–$C_7$ cycloalkyl, $C_1$–$C_4$ monoalkyl substituted $C_5$–$C_7$ cycloalkyl, $C_1$–$C_6$ monohaloalkyl, allyl or the group, —C(O)X, wherein X is a $C_1$–$C_6$ alkyl, phenyl, $C_1$–$C_6$ mono-or $C_1$–$C_6$ di-alkyl substituted phenyl, $C_1$–$C_6$ mono- or $C_1$–$C_6$ di-alkoxy substituted phenyl, $C_1$–$C_6$ alkoxy, phenoxy, $C_1$–$C_6$ mono- or $C_1$–$C_6$ di-alkyl substituted phenoxy, $C_1$–$C_6$ mono- or $C_1$–$C_6$ di-alkoxy substituted phenoxy, $C_1$–$C_6$ alkylamino, phenylamino, $C_1$–$C_6$ mono- or $C_1$–$C_6$ di-alkyl substituted phenylamino, or $C_1$–$C_6$ mono- or $C_1$–$C_6$ di-alkoxy substituted phenylamino and said halo substituent being chloro, fluoro or bromo, provided that one of $R_1$ or $R_2$ is hydrogen;

(b) B is selected from the group consisting of the substituted or unsubstituted aryl groups phenyl and naphthyl, and (c) B' is selected from the group consisting of the substituted or unsubstituted heterocyclic aromatic groups pyridyl, furyl, benzofuryl, thienyl, and benzothienyl, said aryl and heterocyclic substituents being selected from the group consisting of hydroxy, $C_1$–$C_5$ alkyl, $C_1$–$C_5$ haloalkyl, $C_1$–$C_5$ alkoxy, $C_1$–$C_5$ alkoxy($C_1$–$C_4$)alkyl, $C_1$–$C_5$ dialkylamino, acryloxy, methacryloxy, and halogen, said halogen or (halo) groups being fluoro, chloro, or bromo.

14. The photochromic article of claim 13 wherein the organic host material is selected from the group consisting of polyacrylates, cellulose acetate, cellulose triacetate, cellulose acetate propionate, cellulose acetate butyrate, poly(vinyl acetate), poly(vinyl alcohol), poly(vinyl chloride), poly(vinylidene chloride), polycarbonate, polyurethanes, poly(ethylene terephthalate), polystyrene, copoly(styrene-methylmethacrylate), copoly(styrene-acrylonitrile, polyvinylbutyral and polymers of members of the group consisting of polyol(allyl carbonate) monomers, polyfunctional acrylate monomers, and diallylidene pentaerythritol monomers.

15. The photochromic article of claim 14 wherein B is a phenyl group; represented respectively by the following graphic formulae:

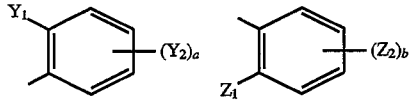

wherein, $Y_1$ is selected from the group consisting of $C_1$–$C_5$ alkyl, $C_1$–$C_5$ alkoxy, fluoro, and chloro, $Z_1$ is selected from the group consisting of hydrogen and $Y_1$, each $Y_2$ and $Z_2$ are selected from the group consisting of $C_1$–$C_5$ alkyl, $C_1$–$C_5$ alkoxy, hydroxy, halogen, acryloxy, and methacryloxy, and a and b are each integers of from 0 to 2.

16. The photochromic article of claim 15 wherein $R_1$ is hydrogen or methyl; $R_2$ is hydrogen or the group, —C(O)W, W being —$OR_4$, wherein $R_4$ is $C_1$–$C_3$ alkyl or allyl; and $R_3$ is hydrogen, $C_1$–$C_3$ alkyl, phenyl($C_1$–$C_3$)alkyl, or the group, —C(O)X wherein X is a $C_1$–$C_4$ alkyl.

17. The photochromic article of claim 16 wherein $Y_1$ is $C_1$–$C_3$ alkyl, $C_1$–$C_3$ alkoxy, or fluoro, $Z_1$ is a hydrogen, each $Y_2$ and $Z_2$ is selected from the group consisting of $C_1$–$C_3$ alkyl and $C_1$–$C_3$ alkoxy, a is the integer 0 or 1, and b is an integer from 0 to 2.

18. The photochromic article of claim 17 wherein the organic host material is a solid transparent homopolymer or copolymer of diethylene glycol bis(allyl carbonate), poly(4, 4'dioxydiphenol-2,2-propane) carbonate, poly(methylmethacrylate), polyvinylbutyral or a polyurethane.

19. The photochromic article of claim 18 wherein the photochromic compound is present in an amount of from about 0.15 to 0.35 milligrams per square centimeter of organic host material surface to which the photochromic compound is incorporated or applied.

20. The photochromic article of claim 19 wherein the weight ratios of the first photochromic substance to the second photochromic substance is from about 1:3 to about 3:1.

21. The photochromic article of claim 20 wherein the article is an ophthalmic lens.

* * * * *